(12) United States Patent
Colen et al.

(10) Patent No.: US 8,137,397 B2
(45) Date of Patent: Mar. 20, 2012

(54) MEDICAL DEVICES

(75) Inventors: Fredericus A. Colen, Maple Grove, MN (US); David Knapp, Shoreview, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 10/787,618

(22) Filed: Feb. 26, 2004

(65) Prior Publication Data

US 2005/0192657 A1   Sep. 1, 2005

(51) Int. Cl.
*A61F 2/06* (2006.01)
(52) U.S. Cl. .................................................. 623/1.42
(58) Field of Classification Search ............... 623/1.4, 623/1.11, 1.13, 1.23, 1.38–1.54, 1.15
See application file for complete search history.

(56) References Cited

U.S. PATENT DOCUMENTS

| | | | |
|---|---|---|---|
| 4,334,327 A * | 6/1982 | Lyman et al. ............. 623/23.66 |
| 4,859,769 A * | 8/1989 | Karlsson et al. ............... 514/25 |
| 4,950,227 A * | 8/1990 | Savin et al. ................. 623/1.12 |
| 5,135,516 A * | 8/1992 | Sahatjian et al. ............. 604/265 |
| 5,317,077 A * | 5/1994 | Kohn et al. ................... 528/182 |
| 5,344,411 A * | 9/1994 | Domb et al. .................. 604/265 |
| 5,356,381 A | 10/1994 | Ensminger et al. |
| 5,383,928 A * | 1/1995 | Scott et al. ................... 623/1.12 |
| 5,476,500 A | 12/1995 | Fain et al. |
| 5,551,954 A * | 9/1996 | Buscemi et al. ............. 623/1.15 |
| 5,576,072 A * | 11/1996 | Hostettler et al. ............. 427/532 |
| 5,587,507 A | 12/1996 | Kohn et al. |
| 5,591,222 A | 1/1997 | Susawa et al. |
| 5,599,352 A | 2/1997 | Dinh et al. |
| 5,605,696 A * | 2/1997 | Eury et al. ..................... 424/423 |
| 5,624,411 A | 4/1997 | Tuch |
| 5,658,327 A | 8/1997 | Altman et al. |
| 5,683,447 A | 11/1997 | Bush et al. |
| 5,693,081 A | 12/1997 | Fain et al. |
| 5,697,967 A | 12/1997 | Dinh et al. |
| 5,716,981 A | 2/1998 | Hunter et al. |
| 5,725,570 A | 3/1998 | Heath |
| 5,735,897 A * | 4/1998 | Buirge ........................ 623/1.15 |
| 5,769,883 A | 6/1998 | Buscemi et al. |
| 5,776,184 A | 7/1998 | Tuch |
| 5,788,979 A | 8/1998 | Alt et al. |
| 5,800,511 A | 9/1998 | Mayer |
| 5,824,048 A | 10/1998 | Tuch |
| 5,830,217 A * | 11/1998 | Ryan ........................... 623/1.11 |
| 5,833,651 A * | 11/1998 | Donovan et al. ............. 604/509 |
| 5,837,007 A | 11/1998 | Altman et al. |
| 5,843,172 A | 12/1998 | Yan |
| 5,869,140 A | 2/1999 | Blohowiak et al. |

(Continued)

FOREIGN PATENT DOCUMENTS

AU    739507    * 4/1998

(Continued)

OTHER PUBLICATIONS

U.S. Appl. No. 10/664,679, filed Sep. 16, 2003, O'Brien et al.*

(Continued)

*Primary Examiner* — Alvin J Stewart
(74) *Attorney, Agent, or Firm* — Fish & Richardson P.C.

(57) ABSTRACT

Medical devices, particularly stents, suitable for drug delivery and including a sugar, sugar derivative, inorganic ionic salt, polysaccharide, amino acid, amino acid derivative, polypeptide, surfactant, or combination thereof, are disclosed.

16 Claims, 4 Drawing Sheets

U.S. PATENT DOCUMENTS

| | | | |
|---|---|---|---|
| 5,873,904 A | 2/1999 | Ragheb et al. | |
| 5,876,756 A * | 3/1999 | Takada et al. | 424/489 |
| 5,888,201 A | 3/1999 | Stinson et al. | |
| 5,899,935 A * | 5/1999 | Ding | 623/1.53 |
| 5,935,506 A | 8/1999 | Schmitz et al. | |
| 5,972,027 A | 10/1999 | Johnson | |
| 5,980,566 A | 11/1999 | Alt et al. | |
| 5,980,972 A * | 11/1999 | Ding | 427/2.24 |
| 6,027,526 A * | 2/2000 | Limon et al. | 623/1.15 |
| 6,071,305 A | 6/2000 | Brown et al. | |
| 6,096,070 A | 8/2000 | Ragheb et al. | |
| 6,099,455 A * | 8/2000 | Columbo et al. | 600/3 |
| 6,099,561 A | 8/2000 | Alt | |
| 6,151,525 A * | 11/2000 | Soykan et al. | 607/50 |
| 6,153,252 A * | 11/2000 | Hossainy et al. | 427/2.3 |
| 6,159,142 A | 12/2000 | Alt | |
| 6,168,602 B1 | 1/2001 | Ryan | |
| 6,180,222 B1 | 1/2001 | Schulz et al. | |
| 6,206,912 B1 * | 3/2001 | Goldsteen et al. | 623/1.23 |
| 6,206,914 B1 * | 3/2001 | Soykan et al. | 623/1.42 |
| 6,212,434 B1 | 4/2001 | Scheiner et al. | |
| 6,214,037 B1 | 4/2001 | Mitchell et al. | |
| 6,240,616 B1 | 6/2001 | Yan | |
| 6,245,104 B1 | 6/2001 | Alt | |
| 6,251,136 B1 * | 6/2001 | Guruwaiya et al. | 623/1.46 |
| 6,253,443 B1 | 7/2001 | Johnson | |
| 6,258,117 B1 * | 7/2001 | Camrud et al. | |
| 6,287,332 B1 | 9/2001 | Bolz et al. | |
| 6,290,722 B1 * | 9/2001 | Wang | 623/1.46 |
| 6,331,186 B1 * | 12/2001 | Wang et al. | 623/1.11 |
| 6,338,739 B1 | 1/2002 | Datta et al. | |
| 6,355,055 B1 * | 3/2002 | Waksman et al. | 623/1.13 |
| 6,358,276 B1 | 3/2002 | Edwin | |
| 6,361,780 B1 | 3/2002 | Ley et al. | |
| 6,368,658 B1 * | 4/2002 | Schwarz et al. | |
| 6,387,121 B1 * | 5/2002 | Alt | |
| 6,391,033 B2 * | 5/2002 | Ryan | |
| 6,395,326 B1 * | 5/2002 | Castro et al. | 427/2.24 |
| 6,413,272 B1 * | 7/2002 | Igaki | 623/1.15 |
| 6,423,092 B2 * | 7/2002 | Datta et al. | |
| 6,447,540 B1 * | 9/2002 | Fontaine et al. | |
| 6,451,050 B1 * | 9/2002 | Rudakov et al. | 623/1.15 |
| 6,475,477 B1 | 11/2002 | Kohn et al. | |
| 6,478,815 B1 * | 11/2002 | Alt | |
| 6,488,701 B1 * | 12/2002 | Nolting et al. | 623/1.13 |
| 6,506,437 B1 | 1/2003 | Harish et al. | |
| 6,530,949 B2 * | 3/2003 | Konya et al. | |
| 6,537,312 B2 | 3/2003 | Datta et al. | |
| 6,545,097 B2 | 4/2003 | Pinchuk et al. | |
| 6,558,733 B1 * | 5/2003 | Hossainy et al. | 427/2.24 |
| 6,589,286 B1 | 7/2003 | Litner | |
| 6,602,287 B1 * | 8/2003 | Millare et al. | |
| 6,613,077 B2 * | 9/2003 | Gilligan et al. | |
| 6,626,933 B1 * | 9/2003 | Lau et al. | 623/1.11 |
| 6,629,992 B2 * | 10/2003 | Bigus et al. | 623/1.12 |
| 6,656,217 B1 * | 12/2003 | Herzog et al. | 623/1.15 |
| 6,656,517 B2 * | 12/2003 | Michal et al. | 427/2.24 |
| 6,663,662 B2 * | 12/2003 | Pacetti et al. | 623/1.13 |
| 6,743,425 B2 * | 6/2004 | Nakao | 424/94.61 |
| 6,764,505 B1 * | 7/2004 | Hossainy et al. | 623/1.15 |
| 6,805,898 B1 * | 10/2004 | Wu et al. | 427/2.25 |
| RE38,653 E | 11/2004 | Igaki et al. | |
| 6,849,089 B2 * | 2/2005 | Stoll | 623/1.42 |
| 6,884,429 B2 | 4/2005 | Koziak et al. | |
| 6,887,270 B2 * | 5/2005 | Miller et al. | 623/11.11 |
| 6,940,580 B2 * | 9/2005 | Winterton et al. | 351/160 H |
| 6,953,560 B1 * | 10/2005 | Castro et al. | 423/423 |
| 6,971,813 B2 * | 12/2005 | Shekalim et al. | 401/208 |
| 7,056,338 B2 * | 6/2006 | Shanley et al. | 623/1.42 |
| 7,060,089 B2 * | 6/2006 | Ley et al. | 623/1.15 |
| 7,083,642 B2 * | 8/2006 | Sirhan et al. | 623/1.42 |
| 7,169,178 B1 * | 1/2007 | Santos et al. | 623/1.42 |
| 7,208,011 B2 * | 4/2007 | Shanley et al. | 623/1.42 |
| 7,247,338 B2 * | 7/2007 | Pui et al. | 427/2.24 |
| 7,438,722 B1 * | 10/2008 | Hossainy | 623/1.42 |
| 7,455,853 B2 * | 11/2008 | Mollison et al. | 424/423 |
| 7,459,468 B2 * | 12/2008 | Haque et al. | 514/345 |
| 7,585,516 B2 * | 9/2009 | Pacetti | 424/424 |
| 7,666,223 B2 * | 2/2010 | Santos et al. | 623/1.42 |
| 7,682,647 B2 * | 3/2010 | Hossainy et al. | 427/2.1 |
| 7,794,776 B1 * | 9/2010 | Limon et al. | 427/2.1 |
| 7,824,440 B2 * | 11/2010 | Santos et al. | 623/1.42 |
| 7,824,441 B2 * | 11/2010 | Santos et al. | 623/1.42 |
| 7,967,855 B2 * | 6/2011 | Furst et al. | 623/1.42 |
| 7,981,150 B2 * | 7/2011 | Scheuermann et al. | 623/1.39 |
| 7,989,018 B2 * | 8/2011 | McNiven et al. | 427/2.1 |
| 2001/0000802 A1 * | 5/2001 | Soykan et al. | 623/1.13 |
| 2001/0013166 A1 * | 8/2001 | Yan | |
| 2001/0021873 A1 * | 9/2001 | Stinson | 623/1.34 |
| 2001/0029660 A1 | 10/2001 | Johnson | |
| 2002/0002353 A1 * | 1/2002 | Michal et al. | 604/265 |
| 2002/0004060 A1 | 1/2002 | Heublein et al. | |
| 2002/0009535 A1 | 1/2002 | Michal et al. | 427/2.1 |
| 2002/0032477 A1 * | 3/2002 | Helmus et al. | |
| 2002/0035394 A1 * | 3/2002 | Fierens et al. | |
| 2002/0123801 A1 * | 9/2002 | Pacetti et al. | |
| 2002/0133224 A1 * | 9/2002 | Bajgar et al. | |
| 2002/0165578 A1 * | 11/2002 | Sawitowski et al. | |
| 2002/0183581 A1 * | 12/2002 | Yoe et al. | 600/3 |
| 2003/0033007 A1 * | 2/2003 | Sirhan et al. | 623/1.42 |
| 2003/0044596 A1 * | 3/2003 | Lazarov et al. | |
| 2003/0068355 A1 * | 4/2003 | Shanley et al. | 424/426 |
| 2003/0083646 A1 * | 5/2003 | Sirhan et al. | 604/891.1 |
| 2003/0088307 A1 * | 5/2003 | Shulze et al. | 623/1.15 |
| 2003/0104028 A1 * | 6/2003 | Hossainy et al. | 424/424 |
| 2003/0114917 A1 * | 6/2003 | Holloway et al. | 623/1.13 |
| 2003/0118649 A1 * | 6/2003 | Gao et al. | 424/471 |
| 2003/0134132 A1 * | 7/2003 | Winterton et al. | 428/451 |
| 2003/0139799 A1 * | 7/2003 | Ley et al. | 623/1.15 |
| 2003/0139801 A1 * | 7/2003 | Sirhan et al. | 623/1.15 |
| 2003/0153983 A1 * | 8/2003 | Miller et al. | 623/23.7 |
| 2003/0158598 A1 * | 8/2003 | Ashton et al. | 623/1.42 |
| 2003/0176884 A1 | 9/2003 | Berrada et al. | |
| 2003/0181973 A1 * | 9/2003 | Sahota | 623/1.15 |
| 2003/0181975 A1 * | 9/2003 | Ishii et al. | 623/1.42 |
| 2003/0232122 A1 * | 12/2003 | Chappa et al. | 427/2.1 |
| 2004/0002752 A1 * | 1/2004 | Griffin et al. | 623/1.15 |
| 2004/0034337 A1 * | 2/2004 | Boulais et al. | 604/890.1 |
| 2004/0054104 A1 * | 3/2004 | Pacetti | 526/242 |
| 2004/0086569 A1 * | 5/2004 | Sparer et al. | 424/486 |
| 2004/0088038 A1 * | 5/2004 | Dehnad et al. | 623/1.15 |
| 2004/0116551 A1 * | 6/2004 | Terry | 523/122 |
| 2004/0148002 A1 * | 7/2004 | Cheng et al. | 623/1.11 |
| 2004/0167610 A1 * | 8/2004 | Fleming, III | 623/1.15 |
| 2004/0191404 A1 * | 9/2004 | Hossainy et al. | 427/2.1 |
| 2004/0204756 A1 * | 10/2004 | Diaz et al. | 623/1.42 |
| 2004/0225346 A1 * | 11/2004 | Mazumder et al. | 623/1.13 |
| 2005/0004661 A1 * | 1/2005 | Lewis et al. | 623/1.42 |
| 2005/0060021 A1 | 3/2005 | O'Brien et al. | |
| 2005/0125051 A1 * | 6/2005 | Eidenschink et al. | 623/1.12 |
| 2005/0187608 A1 * | 8/2005 | O'Hara | 623/1.15 |
| 2005/0233062 A1 * | 10/2005 | Hossainy et al. | 427/2.1 |
| 2006/0069427 A1 * | 3/2006 | Savage et al. | 623/1.16 |
| 2006/0073114 A1 * | 4/2006 | Grainger et al. | 424/85.1 |
| 2006/0094761 A1 * | 5/2006 | Haque et al. | 514/332 |
| 2006/0122697 A1 * | 6/2006 | Shanley et al. | 623/1.42 |
| 2006/0217351 A1 * | 9/2006 | Brandt et al. | 514/165 |
| 2007/0026038 A1 | 2/2007 | Bayer et al. | |
| 2007/0032858 A1 * | 2/2007 | Santos et al. | 623/1.16 |
| 2007/0123977 A1 * | 5/2007 | Cottone et al. | 623/1.42 |
| 2007/0173923 A1 * | 7/2007 | Savage et al. | 623/1.15 |
| 2007/0179599 A1 * | 8/2007 | Brodbeck et al. | 623/1.44 |
| 2007/0207186 A1 * | 9/2007 | Scanlon et al. | 424/424 |
| 2007/0258926 A1 * | 11/2007 | Yamaguchi et al. | 424/69 |
| 2008/0058921 A1 * | 3/2008 | Lindquist | 623/1.42 |
| 2008/0077218 A1 * | 3/2008 | McMorrow et al. | 607/120 |
| 2008/0077230 A1 * | 3/2008 | Heaney et al. | 623/1.15 |
| 2008/0097577 A1 * | 4/2008 | Atanasoska et al. | 623/1.15 |
| 2008/0147177 A1 * | 6/2008 | Scheuermann et al. | 623/1.42 |
| 2008/0234810 A1 * | 9/2008 | Carlson et al. | 623/1.42 |
| 2008/0243231 A1 * | 10/2008 | Flanagan et al. | 623/1.16 |
| 2008/0287370 A1 * | 11/2008 | Madge et al. | 514/18 |
| 2009/0005861 A1 * | 1/2009 | Hossainy et al. | 623/1.46 |
| 2009/0048270 A1 * | 2/2009 | Koehler et al. | 514/256 |
| 2009/0062904 A1 * | 3/2009 | Furst | 623/1.15 |
| 2009/0099183 A1 * | 4/2009 | Bhatt et al. | 514/235.8 |
| 2009/0192593 A1 * | 7/2009 | Meyer et al. | 623/1.42 |

| | | | | |
|---|---|---|---|---|
| 2010/0021523 A1* | 1/2010 | Scheuermann et al. | | 424/423 |
| 2010/0106242 A1* | 4/2010 | Ozkan et al. | | 623/1.42 |
| 2010/0136213 A1* | 6/2010 | Hossainy et al. | | 427/2.25 |
| 2011/0001271 A1* | 1/2011 | Hossainy et al. | | 264/345 |
| 2011/0008528 A1* | 1/2011 | Santos et al. | | 427/2.24 |
| 2011/0066227 A1* | 3/2011 | Meyer et al. | | 623/1.42 |
| 2011/0166249 A1* | 7/2011 | Ippoliti et al. | | 523/113 |
| 2011/0189255 A1* | 8/2011 | Sturek et al. | | 424/423 |
| 2011/0214785 A1* | 9/2011 | Buckman et al. | | 148/237 |

FOREIGN PATENT DOCUMENTS

| | | | |
|---|---|---|---|
| CA | 2235031 | * | 4/1998 |
| CA | 2346857 | | 5/2000 |
| CA | 2371800 | | 8/2000 |
| EP | 0337035 B1 | | 11/1993 |
| EP | 1 222 901 | | 7/2002 |
| EP | 1273314 | | 1/2003 |
| EP | 1260214 | | 6/2004 |
| WO | WO 98/48851 | | 11/1998 |
| WO | 99/30772 | | 6/1999 |
| WO | WO 99/64580 | | 12/1999 |
| WO | WO 00/25841 | | 5/2000 |
| WO | WO 00/48660 | | 8/2000 |
| WO | WO 00/51136 | | 8/2000 |
| WO | WO 00/66190 | | 11/2000 |
| WO | WO02/47739 | | 6/2002 |
| WO | WO03/035131 | | 5/2003 |
| WO | WO03/094990 | | 11/2003 |

OTHER PUBLICATIONS

"Anodizing and Its Uses" Available Web Site: www.anodizing.org/AAC_FactSheet1v2.pdf Retrieved from the interni prior to the filing of the application.

"Anodizing Reference Guide" Available Web Site: www.anodizing.org/reference_guide.html Retrieved from the internet prior to the filing of the application.

"Current Anodizing Processes" Available Web Site: www.anodizing.org/processes.html Retrieved from the internet prior to the filing of the application.

"Anodizing . . . The Finish of Choice" Available Web Site: www.anodizing.org/what_is_anodizing.html Retrieved from the internet prior to the filing of the application.

"Anodizing, What Is It?" Available Web Site: www.anodizing.org/definitons.html Retrieved from the internet prior to the filing of the application.

"Anodization of Titanium for Biocompatibility" Available Web Site: www.finishing.com/70/68.html Retrieved from the internet prior to the filing of the application.

"Bike Pro Buyer's Guide" Available Web Site: www.bikepro.com/products/metals/alum.html Retrieved from the internet prior to the filing of the application.

"More on Anodizing Aluminum" Available Web Site: www.turborick.com/anodize2.html Retrieved from the internet prior to the filing of the application.

List of Abstracts of References [online], 57 pages. Retrieved from: the Thomson Derwent World Patent Index.

List of Abstracts of References [online], 8 pages. Retrieved from: the Thomsn Derwent World Patent Index.

"Best of the ACC Scientific Session 2002", *Rev Cardiovasc Med.* 2002:3(2):p. 85-104.

Brandau, W. et al., "Nanoporous Ceramic Coatings for Synthesis of Radioactive Implants," *Journal of Nuclear Medicine Abstract Book*, Jun. 7, 2000, p. 244P.

Dunn, D.S. et al., "Anodized Layers on Titanium and Titanium Alloy Orthopedic Materials for Antimicrobial Activity Applications," *Materials & Manufacturing Processes*, 7(1), p. 123-137 (1992).

Sawitowski, T. et al., "Nanoporous Alumina Coatings for Medical Implants and Stents—Radiotherapy, Drug Delivery, Biological Compatibility," Materials Research Society Symposium Proceedings, vol. 581 (1999), p. 523-528.

Sawitowski, T., "New Drug Delivery Systems—Examples of Applied Nanotechnology," VDE World Microtechnologies Congress, Sep. 25-27, 2000, Expo 2000, Hannover, Germany, Proveeds vol. 1, p. 343-346.

Wieneke, H. et al., "Stent Coating: A New Approach in Interventional Cardiology," Herz 27,No. 6., (2002), p. 518-526.

International Search Report and Written Opinion for International Application No. PCT/US2005/005630, mailed Jun. 22, 2005.

\* cited by examiner

MEDICAL DEVICES

TECHNICAL FIELD

This invention relates to medical devices, particularly endoprostheses.

BACKGROUND

The body includes various passageways such as arteries, other blood vessels, and other body lumens. For various treatments and diagnostic techniques, it is often desirable to deliver a medical device into these lumens. For example, these passageways sometimes become occluded or weakened. The passageways can be occluded by e.g. a tumor, restricted by plaque, or weakened by an aneurysm. When this occurs, the passageway can be reopened or reinforced, or even replaced, with a medical endoprosthesis. An endoprosthesis is typically a tubular member that is placed in a lumen in the body. Examples of endoprostheses include stents and covered stents, sometimes called "stent-grafts". An endoprosthesis can be delivered inside the body by a catheter that supports the endoprosthesis in a compacted or reduced-size form as the endoprosthesis is transported to a desired site. Upon reaching the site, the endoprosthesis is expanded, for example, so that it can contact the walls of the lumen. The expansion mechanism may include forcing the endoprosthesis to expand radially. For example, the expansion mechanism can include the catheter carrying a balloon, which carries the endoprosthesis. The balloon can be inflated to deform and to fix the expanded endoprosthesis at a predetermined position in contact with the lumen wall. The balloon can then be deflated, and the catheter removed.

In another delivery technique, the endoprosthesis is self-expanding. For example, the endoprosthesis can be formed of an elastic material that can be reversibly compacted and expanded. During introduction into the body, the endoprosthesis is restrained in a compacted condition. Upon reaching the desired implantation site, the restraint is removed, for example, by retracting a restraining device such as an outer sheath, enabling the endoprosthesis to self-expand by its own internal elastic restoring force. Another self-expansion technique uses shape memory metals which can "remember" a particular geometric configuration, e.g. an expanded condition, upon exposure to a trigger, such as an increase in temperature.

The endoprosthesis can carry a drug, such as an antiproliferative, to reduce the likelihood of restenosis, i.e., reclosure of the vessel due to immune reactions by the body at the treatment site.

SUMMARY

In one aspect, the invention features a medical stent with a generally tubular body. The medical stent also includes a therapeutic agent, and a sugar, sugar derivative, or inorganic ionic salt.

In another aspect, the invention features a stent delivery system that includes a catheter with a balloon and a medical stent device, and that has a generally tubular body, a therapeutic agent, and a sugar, sugar derivative, or inorganic ionic salt.

In another aspect, the invention features a stent delivery system that includes a catheter with a retractable sheath and a medical stent device, and that has a generally tubular body, a therapeutic agent, and a sugar, sugar derivative, or inorganic ionic salt.

In another aspect, the invention features a medical stent with a generally tubular body and a sugar, sugar derivative, or inorganic ionic salt.

In another aspect, the invention features a method of making a coated stent, the method including providing a stent, providing a therapeutic agent, and coating the stent with a layer of sugar, sugar derivative, or inorganic ionic salt.

In various aspects, the invention includes an implantable medical device (e.g., a stent) that includes an implantable body, a therapeutic agent and a sugar, sugar derivative, inorganic ionic salt, surfactant, polysaccharide, polypeptide, amino acid, amino acid derivative, or a combination thereof.

Embodiments can include one or more of the following features.

The sugar, sugar derivative, or salt can have a solubility of at least 0.14 gram/mL of water, and/or a melting point of about 47° C. or more. The stent can include a sugar or a sugar derivative (e.g., sucrose, sorbose, glucosamine, mannitol). The stent can include an inorganic ionic salt (e.g., sodium chloride, potassium chloride, sodium carbonate). The stent can have a layer that includes a therapeutic agent and the sugar, sugar derivative, or salt. The stent can have a layer of sugar, sugar derivative, or salt that covers a therapeutic agent-containing reservoir. The reservoir can be a layer of therapeutic agent. The reservoir can define pores in which the therapeutic agent can be disposed. The reservoir can include metal that is integral with the stent body. The stent can further include a second therapeutic agent that is carried by the layer, and the second therapeutic agent can be different from the therapeutic agent that is carried by the reservoir. The therapeutic agent can be an antithrombogenic, an antioxidant, an anti-inflammatory, an antiproliferative, and/or an antibiotic. The stent can be a self-expanding stent or a balloon-expandable stent. The stent can be a vascular stent. Coating can include dip coating and/or spray coating. Coating can include forming a preform layer and fixing the preform layer to the stent. The perform layer can be fixed by applying a solution of, or a liquid form of, a sugar, sugar derivative, or to the stent.

Embodiments of the invention can have one or more of the following advantages. The protective layer can prevent the therapeutic agent from being exposed to or released into the body until it has reached its target site. The layer is highly bioerodible and water-soluble, such that it rapidly dissolves when the treatment site is reached. The layer can be flexible, such that it can be moved through a tortuous lumen and expanded as the strut expands without significant fracture, flaking, or disruption. Furthermore, the protective layer is the same as, or chemically analogous to, substances that are either commonly present in the body, or that the body regards as non-foreign. As a result, the protective layer generally is not of a material type that elicits an adverse reaction by the body, such as inflammation or an autoimmune response. The layer material typically is easily metabolized. In addition, the protective layer does not adversely interact with the drug during storage or during delivery. The layer can be relatively inexpensive and readily commercially available.

Still further aspects, features, and advantages follow.

DETAILED DESCRIPTION

Figure 1A:
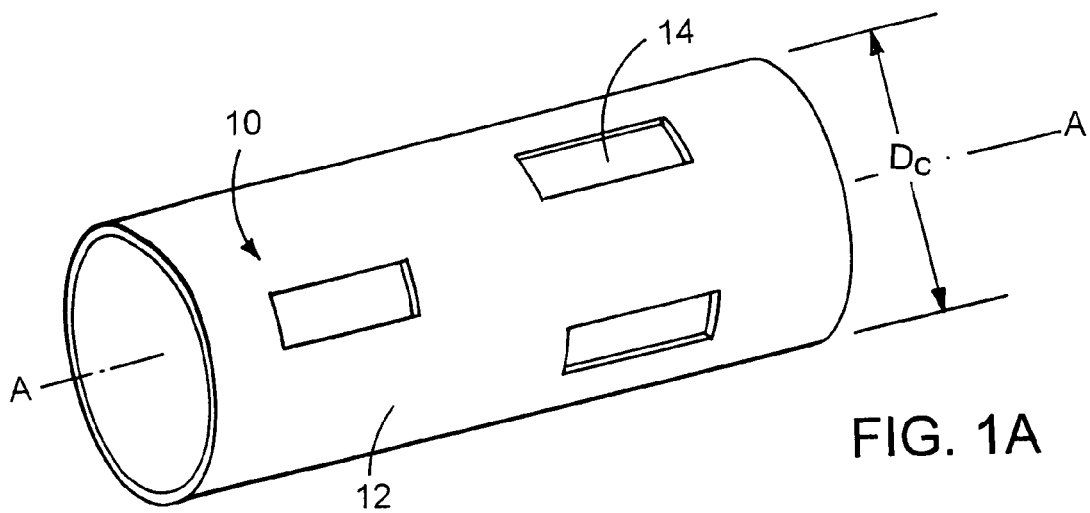
FIGS. 1A and 1B are perspective views of a stent in the compressed and expanded condition, respectively.
Figure 1B:
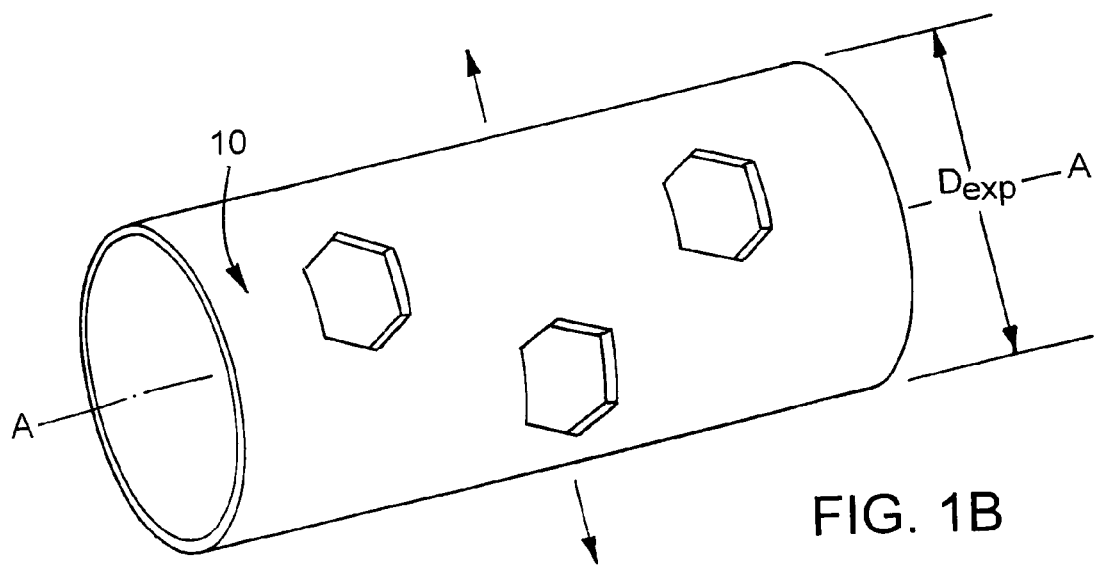

Referring to FIGS. 1A and 1B, a stent 10 includes a generally tubular body 12. The tubular body includes aperture regions 14 provided in a pattern to facilitate stent functions, such as radial expansion and lateral flexibility. Referring particularly to FIG. 1A, for delivery into the body, the stent 10 is provided or maintained in a relatively small diameter condition corresponding to a diameter $D_c$. Referring to FIG. 1B, upon delivery to the treatment site, the stent 10 is expanded to a larger diameter, $D_{exp}$, so that the stent is in contact with the lumen wall. The stent may be expanded by a mechanical expander, such as an inflatable balloon, or it may be self-expanding. The body of the stent may be formed by a generally continuous sheet or by filaments that are wrapped, braided, knitted or otherwise configured to generally define a stent. The stent is delivered into the body on a catheter, such as a balloon catheter. The catheter can include a retractable sheath that concentrically surrounds the stent during delivery and is retracted during employment at the treatment site. Alternatively, the stent may be exposed to the body lumen during delivery. A suitable stent design is the Express stent, available from Boston Scientific, Natick, Mass. Balloon expandable and self-expanding stents and delivery systems are further discussed in Heath, U.S. Pat. No. 5,725,570, the entire contents of which are incorporated herein by reference.

Figure 2:
FIG. 2 is a greatly enlarged cross-section through the side wall of a stent.

Referring now to FIG. 2, a cross-section through the stent side wall, the stent 10 includes a body 20 onto which are provided a drug reservoir 22 and a protective layer 24. The body 20 is formed of material capable of performing the expansion function of the stent. For example, the body 20 may be a highly elastic metal, in the case of a self-expanding stent, or a plastically deformable metal, in the case of a balloon-expandable stent. The drug reservoir 22 contains a therapeutic agent to be released in the body during use of the stent. The protective layer 24 covers the drug reservoir prior to and, if desirable, during the delivery and implantation of the stent into the body. For example, the protective layer protects the reservoir from abrasion during packaging, shipping, unpacking, and delivery. The protective layer can be removed prior to delivery into the body. Alternatively, the protective layer can also protect the reservoir from premature exposure to body fluid during delivery.

The protective layer can be made of a sugar, a sugar derivative, a simple inorganic ionic salt, or a combination thereof. These material(s) are chemically the same as, or analogous to, substances that are commonly present in the body and material types that typically do not cause adverse reactions, such as inflammation, or that do not interact adversely with the drug or reservoir. The protective layer preferably erodes at a relatively rapid rate, so that the therapeutic agent can be released into the body at the appropriate time, i.e., when the endoprosthesis reaches the target site. Preferably, the protective layer will dissolve within about 10 to 30 minutes after contact with bodily fluids. The protective layer preferably has a solubility of at least about 0.14 gram/mL of water at about 25° C. (unless otherwise noted, all of the following solubility values are at about room temperature, i.e., about 25° C.). Additionally, the protective layer preferably is flexible, such that it can be maneuvered within the lumen relatively easily. The protective layer preferably is a material that is relatively robust to abrasion, so that it can withstand friction created by contact with the lumen wall or the sheath of the catheter, for example. The protective layer maintains its structural integrity while it is passing through the body; i.e., the protective layer should not undergo substantial plastic or elastic deformation as it is dissolving. Deformation can be minimized by selecting protective layer materials with melting points substantially above, e.g. about 10° C. or 50° C. or more, normal body temperature (about 37° C.).

Suitable sugars are carbohydrates composed of polyhydroxy aldehydes and ketones and their derivatives. Examples of suitable sugars include sucrose ($C_{12}H_{22}O_{11}$), dextrose ($C_6H_{12}O_6$), and sorbose ($C_6H_{12}O_6$). Sucrose has a solubility of about 2 grams/mL of water and a melting point of about 185-186° C. Dextrose has a solubility of about 1 gram/mL of water and a melting point of about 146-150° C. Sorbose is freely soluble in water and has a melting point of about 162-165° C.

Suitable sugar derivatives include sugar alcohols, such as polyhydric alcohols having no more than one hydroxy group attached to each carbon atom, formed by the reduction of the carbonyl group of a sugar to a hydroxyl group. A suitable sugar alcohol is mannitol ($C_6H_{14}O_6$). Mannitol has a solubility of about 0.18 gram/mL of water and a melting point of about 168° C. Another example of a sugar derivative is glucosamine ($C_6H_{13}NO_5$), an amino derivative of glucose.

Suitable inorganic ionic salts include salts containing a cation and an anion, where the cation is an alkali or alkaline earth metal, and the anion is a halide or a polyatomic ion. Examples of suitable salts include sodium chloride (NaCl), potassium chloride (KCl), and sodium carbonate ($Na_2CO_3$). Sodium chloride has a solubility of about 0.36 gram/mL of water and a melting point of about 804° C. Potassium chloride has a solubility of about 0.36 gram/mL of water and a melting point of about 773° C.

In embodiments, the protective layer can be made of a polysaccharide (e.g., starch, dextran, cyclodextrin), an amino acid, an amino acid derivative, a polypeptide, a surfactant (e.g., phosphatidylcholine, a Tween® surfactant, or a lipid), or a combination thereof.

The thickness of the protective layer can be selected on the basis of the protective layer's solubility and the desired dissolution time of the protective layer. Protective layers that are highly soluble can be thicker than those protective layers that are more insoluble. In embodiments, the protective layer has a thickness of from about 0.1 micron to about 20 microns. In embodiments, the protective layer dissolves en route to the target site or it may dissolve once the stent has reached the target site. In some cases, the protective layer partially dissolves en route to the target site, and finishes dissolution once the stent has reached the target site.

The protective layer can be applied to the stent by techniques including spraying and dip coating. The protective layer can also be preformed, e.g. by casting. The preformed protective layer can be applied to the stent by an adhesive layer, e.g. the molten or solubilized material of the protective layer itself (in the case of mannitol), or a heated syrup of fructose and sucrose which solidifies upon cooling, or syrups of other sugars or sugar derivatives (such as mannitol or sorbitol).

The drug reservoir can take several different forms. For example, the drug layer can be a layer of the drug itself, solidified on the surface of the stent. Alternatively or additionally, the drug can be contained in a reservoir defined by a different material, e.g. a polymer, that is also bioerodible and/or functions as a time-release membrane. For example, the reservoir can be formed of the materials suitable for the protective layer discussed above. A drug reservoir can be formed by a stent body that has an integral porous surface. The porous surface can be formed by machining, laser drilling, sintering or anodization. Sintering is a process by which metal particles are bonded together without being entirely melted. Rather, the particles are pressed together or molded into a certain shape via pressure. Then, the particles are heated to a point just below their melting point. The particles do not melt per se; instead, the particles bond together at their surfaces. The result is that spaces (i.e., "pores") remain between the bonded particles.

Figure 3:
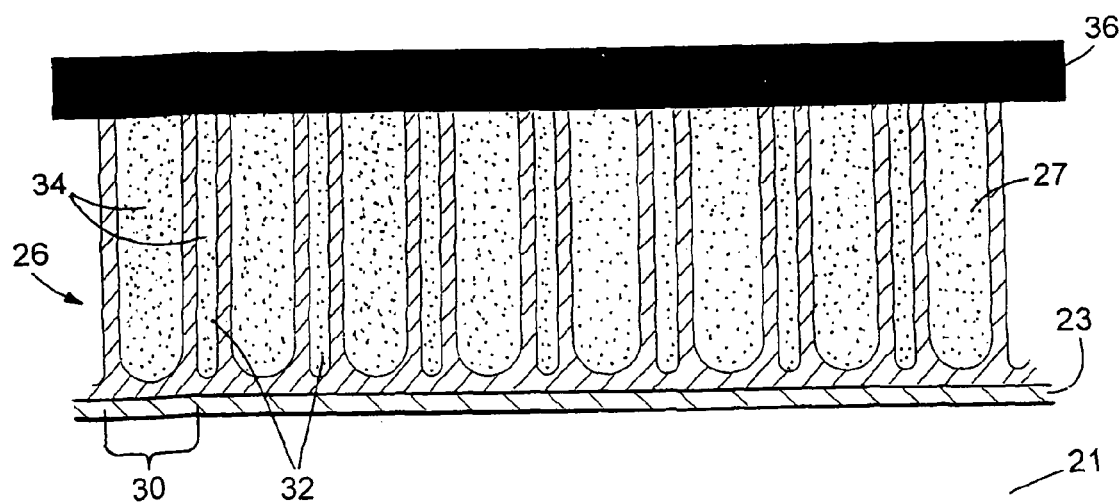
FIG. 3 is a greatly enlarged cross-section through a side wall of a stent.

Anodization is an electrolytic oxidation of a metal. For certain metals, such as aluminum, anodization creates a morphology of post-shaped elements on the surface of the metal, which can enhance strength. As a result, a porous structure can be formed generally without sacrificing the strength of the metal or impeding the function of the medical device. Referring to FIG. 3, greatly enlarged cross-section through a side wall of a stent, the stent side wall is composed of a base material 21, an intermediate layer 23, and a porous layer 26. The morphology of porous layer 26, which is formed by anodization, is a generally regular array of hollow post-shaped elements 30 defining internal volumes 27. Void regions 32 are defined between hollow post-shaped elements 30. A therapeutic agent 34 fills internal volumes 27 and void regions 32. A protective layer 36 covers porous layer 26 in order to prevent therapeutic agent 34 from being dispersed into the body before the stent has reached the target site. Anodization can be carried out directly on the stent body or a coating of a suitable anodizeable metal can be provided over the stent body. Anodization and stents with anodized surfaces are described, for example, in U.S. patent application Ser. No. 10/664,679, filed Sep. 16, 2003, and entitled "Medical Devices", the entire contents of which are incorporated by reference herein.

The term "therapeutic agent" includes one or more "therapeutic agents" or "drugs". The terms "therapeutic agents" and "drugs" are used interchangeably and include pharmaceutically active compounds, nucleic acids with and without carrier vectors such as lipids, compacting agents (such as histones), virus (such as adenovirus, adeno-associated virus, retrovirus, lentivirus and a-virus), polymers, antibiotics, hyaluronic acid, gene therapies, proteins, cells, stem cells and the like, or combinations thereof, with or without targeting sequences. Specific examples of therapeutic agents include, for example, pharmaceutically active compounds, proteins, cells, stem cells, oligonucleotides, ribozymes, antisense oligonucleotides, DNA compacting agents, gene/vector systems (i.e., any vehicle that allows for the uptake and expression of nucleic acids), nucleic acids (including, for example, recombinant nucleic acids; naked DNA, cDNA, RNA; genomic DNA, cDNA or RNA in a noninfectious vector or in a viral vector and which further may have attached peptide targeting sequences; antisense nucleic acid (RNA or DNA); and DNA chimeras which include gene sequences and encoding for ferry proteins such as membrane translocating sequences ("MTS") and herpes simplex virus-1 ("VP22")), and viral, liposomes and cationic and anionic polymers and neutral polymers that are selected from a number of types depending on the desired application. Non-limiting examples of virus vectors or vectors derived from viral sources include adenoviral vectors, herpes simplex vectors, papilloma vectors, adeno-associated vectors, retroviral vectors, and the like. Non-limiting examples of biologically active solutes include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents and factors; agents blocking smooth muscle cell proliferation such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/anti-proliferative/anti-mitotic agents such as paclitaxel, 5-fluorouracil, methotrexate, doxorubicin, daunorubicin, cyclosporine, cisplatin, vinblastine, vincristine, epothilones, endostatin, angiostatin and thymidine kinase inhibitors; anti-microbials such as triclosan, dephalosporins, aminoglycosides, and nitorfurantoin; anesthetic agents such as lidocaine, buplvacaine, and ropivacaine; nitrix oxide (NO) donors such as lisidomine, molsidomine, L-argine, NO-protein adducts, NO-carbohydrate adducts, polymeric or oligomeric NO adducts; anti-coagulants such as D-Phe-Pro-Arg chloromethyl ketone, an RGD peptide-containing compound, heparine, antithrombin compounds, platelet receptor antagonists, anti-thrombin antibodies, anti-platelet receptor antibodies, enoxaparin, hirudin, Warafin sodium, Dicumarol, aspirin, prostaglandin inhibitors, platelet inhibitors and tick antiplatelet factors; vascular cell growth promoters such as growth factors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifinctional molecules consisting of an antibody and a cytotoxin; cholesterol-lowering agents; vasodilating agents; agents which interfere with endogenous vascoactive mechanisms; survival genes which protect against cell death, such as anti-apoptotic Bcl-2 family factors and Akt kinase; and combinations thereof. Cells can be of human origin (autologous or allogenic) or from an animal source (xenogeneic), genetically engineered if desired to deliver proteins of interest at the injection site. The delivery mediated is formulated as needed to maintain cell function and viability.

In some cases, the protective layer may contain a drug, which may be the same as or different from the drug in the reservoir. For example, the protective layer may include one type of drug, e.g. an antithrombogenic agent which is released quickly during delivery and deployment, while the reservoir may contain a different type of drug, e.g. an anti-inflamimatory which is released more slowly at the site.

Figure 4A:
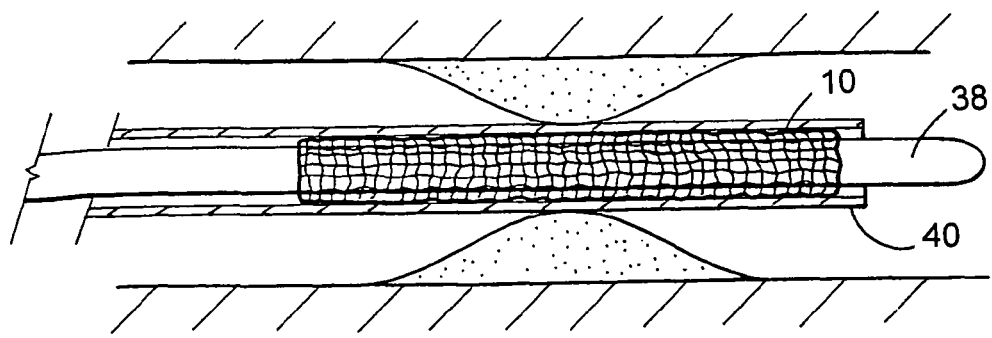
FIGS. 4A-4C are a schematic representation of a stent delivery.
Figure 4B:
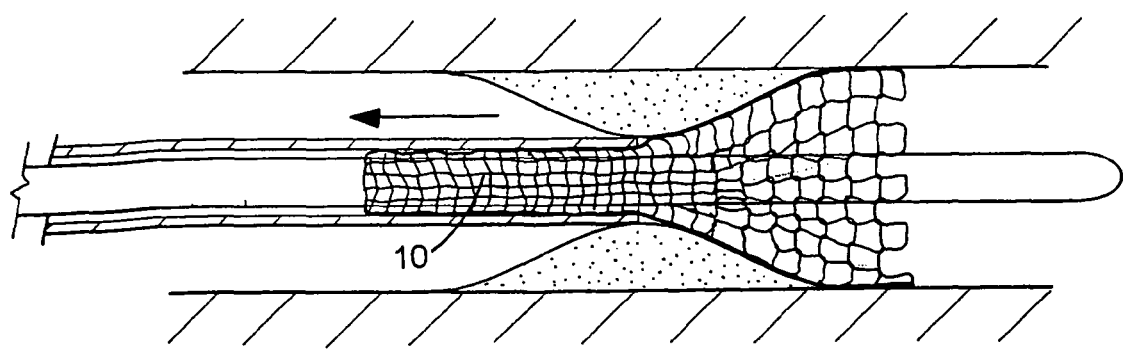
Figure 4C:
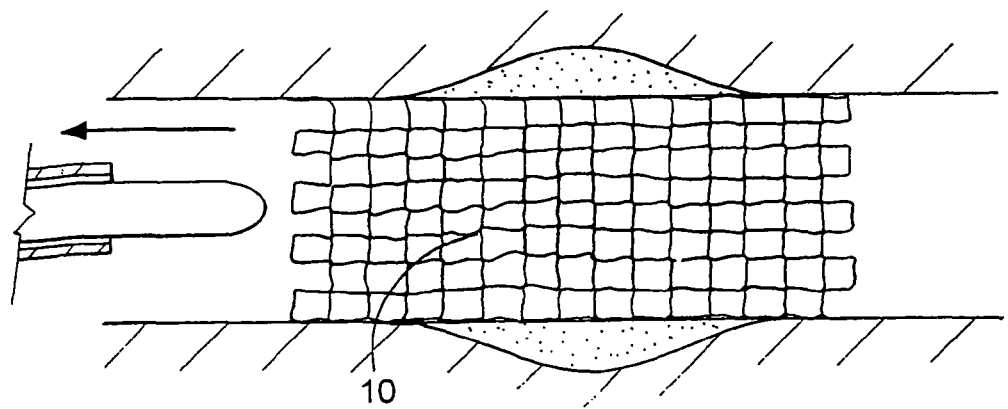
Figure 5A:
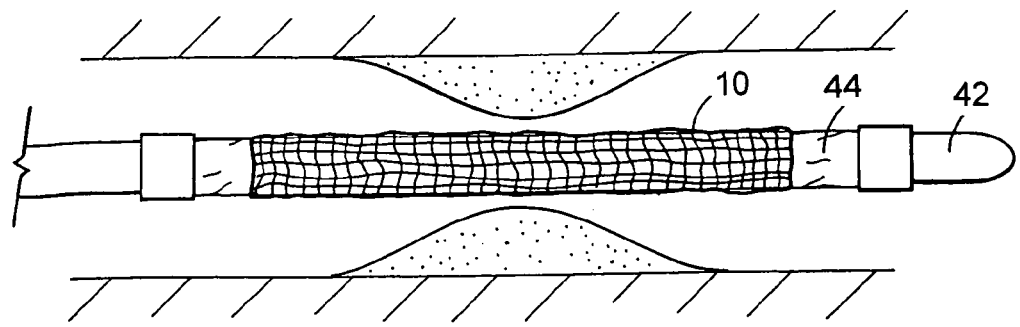
FIGS. 5A-5C are another schematic representation of a stent delivery.
Figure 5B:
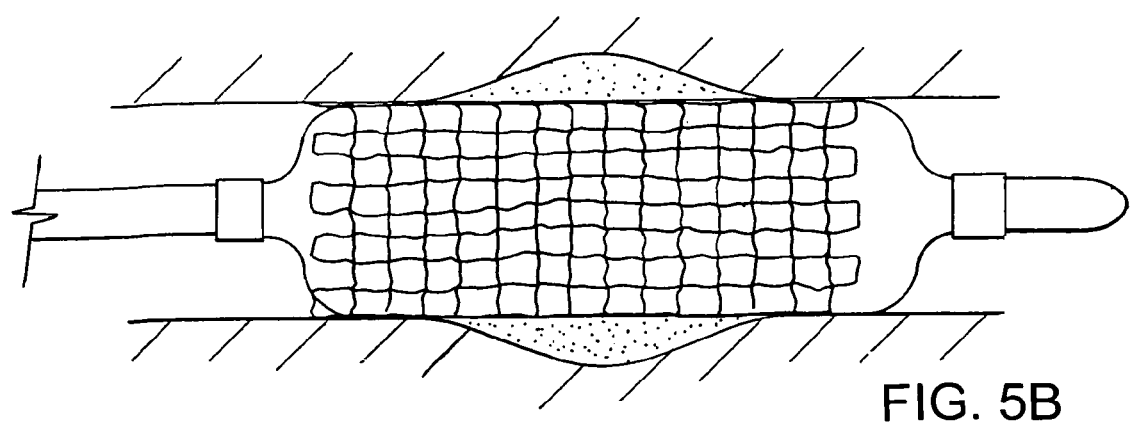
Figure 5C:
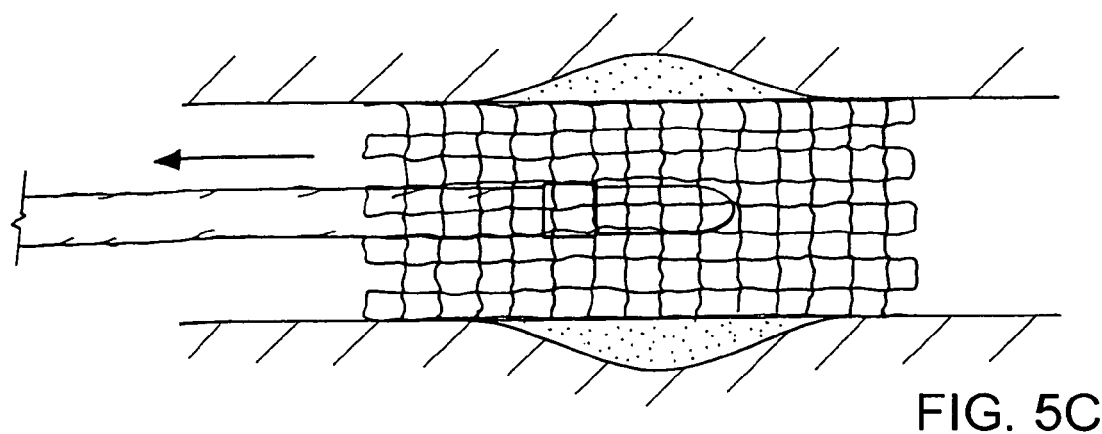

As discussed above, the stent body may be made out of any of a number of different materials. Referring to FIGS. 4A-4C, the delivery of a self-expanding stent is illustrated. The stent 10 is deployed on a catheter 38 and covered by a sheath 40. When the target site is reached, the sheath is retracted and the stent self-expands into contact with the body lumen. Referring now to FIGS. 5A-5C, the delivery of a balloon-expandable stent is illustrated. The stent 10 is carried on a catheter 42 over a balloon 44. When the treatment site is reached, the balloon is expanded to expand the stent into contact with the lumen wall. The stent body may be made of, for example, Nitinol, a nickel-titanium alloy that can provide stent with superelasticity and shape memory properties. In some cases, the stent body may be made of stainless steel (e.g., 300 series stainless steel), or aluminum. The stent body may be made of composite materials as described in Heath, U.S. Pat. No. 5,725,570, and Mayer, U.S. Pat. No. 5,800,511. A stent as described above has many different possible applications. For example, the stent may be used in the vascular system (e.g., in the coronary arteries), or in the gastrointestinal tract. The stent may be an esophageal stent. The stent may be used in the biliary duct, or in other body lumens.

While a stent has been described above, a protective layer and a drug-containing reservoir may be applied to other implantable medical devices, and particularly to implantable medical devices that are suitable for drug delivery. For example, they may be used in guidewires, catheters (including balloon angioplasty catheters), or filters (including vena cava filters).

Still other embodiments are possible. For example, where the protective layer material itself has a desirable therapeutic effect, e.g. if delivery of a sugar or salt to a treatment site is desired, the protective layer material can be applied to a stent that does not include a drug reservoir.

All publications, applications, references, and patents referred to above are incorporated by reference in their entirety.

Other embodiments are within the following claims.

What is claimed is:

1. A medical stent, comprising:
a generally tubular body;
a reservoir containing a first therapeutic agent; and
a body-fluid dissolvable protective layer disposed over the generally tubular body, the layer consisting essentially of an inorganic ionic salt selected from the group consisting of sodium chloride, potassium chloride, and sodium carbonate,
wherein
the layer covers the reservoir, and
the reservoir is formed of a bioerodible material.

2. The medical stent of claim 1 wherein the layer includes a second therapeutic agent.

3. The medical stent of claim 2 wherein the second therapeutic agent is different from the first therapeutic agent.

4. The medical stent of claim 1 wherein the reservoir is a layer of the first therapeutic agent.

5. The medical stent of claim 1 wherein the reservoir defines pores and the first therapeutic agent is disposed within the pores.

6. The medical stent of claim 1 wherein the reservoir comprises metal integral with the stent body.

7. The medical stent of claim 1 wherein the first therapeutic agent is selected from an group consisting of an antithrombogenic, antioxidant, anti-inflammatory, antiproliferative, or antibiotic.

8. The medical stent of claim 1 wherein the stent is a self-expanding stent.

9. The medical stent of claim 1 wherein the stent is a balloon-expandable stent.

10. The medical stent of claim 1 wherein the stent is a vascular stent.

11. The medical stent of claim 1, wherein the layer consists of an inorganic ionic salt selected from the group consisting of sodium chloride, potassium chloride, and sodium carbonate.

12. The implantable medical device of claim 11, wherein the bioerodible material comprises a bioerodible polymer.

13. The medical stent of claim 1 wherein the bioerodible material comprises a bioerodible polymer.

14. An implantable medical device, comprising:
an implantable body;
a reservoir containing a therapeutic agent; and
a body-fluid dissolvable protective layer disposed over the implantable body, the layer consisting essentially of an inorganic ionic salt selected from the group consisting of sodium chloride, potassium chloride, and sodium carbonate,
wherein
the layer covers the reservoir, and
the reservoir is formed of a bioerodible material.

15. The implantable medical device of claim 14, wherein the implantable medical device is a balloon angioplasty catheter.

16. An implantable medical device, of claim 14, wherein the bioerodible material comprises a bioerodible polymer.

* * * * *

UNITED STATES PATENT AND TRADEMARK OFFICE
CERTIFICATE OF CORRECTION

PATENT NO.         : 8,137,397 B2
APPLICATION NO.    : 10/787618
DATED              : March 20, 2012
INVENTOR(S)        : Fredericus A. Colen and David Knapp It is certified that error appears in the above-identified patent and that said Letters Patent is hereby corrected as shown below:

1.) Column 7, Claim 3, Lines 35-36: delete the entire claim and replace it with the following claim
--The medical stent of claim 1 wherein the reservoir is a layer of the first therapeutic agent.--.

2.) Column 7, Claim 4, Lines 37-38: delete the entire claim and replace it with the following claim
--The medical stent of claim 1 wherein the reservoir defines pores and the first therapeutic agent is disposed within the pores.--.

3.) Column 8, Claim 5, Lines 1-3: delete the entire claim and replace it with the following claim
--The medical stent of claim 1 wherein the reservoir comprises metal integral with the stent body.--.

4.) Column 8, Claim 6, Lines 4-5: delete the entire claim and replace it with the following claim
--The medical stent of claim 2 wherein the second therapeutic agent is different from the first therapeutic agent.--.

5.) Column 8, Claim 7, Line 7: delete "from an", and insert --from the--.

6.) Column 8, Claim 7, Line 8: delete "or" and insert --the--.

7.) Column 8, Claim 11, Lines 16-19: delete the entire claim and replace it with the following claim
--An implantable medical device, comprising:
an implantable body;
a reservoir containing a therapeutic agent; and
a body-fluid dissolvable protective layer disposed over the implantable body, the layer consisting essentially of an inorganic ionic salt selected from the group consisting of sodium chloride, potassium chloride, and sodium carbonate,
wherein
the layer covers the reservoir, and Signed and Sealed this
Fifteenth Day of January, 2013

David J. Kappos
*Director of the United States Patent and Trademark Office*

CERTIFICATE OF CORRECTION (continued)

U.S. Pat. No. 8,137,397 B2 the reservoir is formed of a bioerodible material.--.

8.) Column 8, Claim 12, Lines 20-21: delete the entire claim and replace it with the following claim
    --The medical stent of claim 1, wherein the layer consists of an inorganic ionic salt
selected from the group consisting of sodium chloride, potassium chloride, and sodium
carbonate.--.

9.) Column 8, Claim 14, Lines 24-34: delete the entire claim and replace it with the following claim
    --The implantable medical device of claim 11, wherein the implantable medical device is a
balloon angioplasty catheter.--.

10.) Column 8, Claim 15, Lines 35-37: delete the entire claim and replace it with the following claim
    --The implantable medical device of claim 14, wherein the bioerodible material comprises
a bioerodible polymer.--.

11.) Column 8, Claim 16, Line 38: delete "an", and insert --the--.

12.) Column 8, Claim 16, Line 38: delete "claim 14", and insert --claim 12--.